(12) United States Patent
Ohshiro et al.

(10) Patent No.: US 8,980,922 B2
(45) Date of Patent: Mar. 17, 2015

(54) 5-HT4 RECEPTOR AGONISTS FOR THE TREATMENT OF DEMENTIA

(75) Inventors: Hiroyuki Ohshiro, Aichi (JP); Akiyoshi Fujiuchi, Aichi (JP); Yukinori Take, Aichi (JP)

(73) Assignee: Raqualia Pharma Inc., Aichi (JP)

( * ) Notice: Subject to any disclaimer, the term of this patent is extended or adjusted under 35 U.S.C. 154(b) by 0 days.

(21) Appl. No.: 13/578,127

(22) PCT Filed: Feb. 14, 2011

(86) PCT No.: PCT/JP2011/000793
§ 371 (c)(1),
(2), (4) Date: Aug. 30, 2012

(87) PCT Pub. No.: WO2011/099305
PCT Pub. Date: Aug. 18, 2011

(65) Prior Publication Data
US 2012/0322826 A1    Dec. 20, 2012

Related U.S. Application Data

(60) Provisional application No. 61/282,432, filed on Feb. 12, 2010.

(51) Int. Cl.
| A61K 31/454 | (2006.01) |
| A61P 25/28 | (2006.01) |
| C07D 405/14 | (2006.01) |
| C07D 211/26 | (2006.01) |
| C07D 401/12 | (2006.01) |
| C07D 401/14 | (2006.01) |
| C07D 403/12 | (2006.01) |
| C07D 405/06 | (2006.01) |
| C07D 413/14 | (2006.01) |

(52) U.S. Cl.
CPC ............ *C07D 405/14* (2013.01); *A61K 31/454* (2013.01); *C07D 211/26* (2013.01); *C07D 401/12* (2013.01); *C07D 401/14* (2013.01); *C07D 403/12* (2013.01); *C07D 405/06* (2013.01); *C07D 413/14* (2013.01)
USPC ....................................................... 514/322

(58) Field of Classification Search
None
See application file for complete search history.

(56) References Cited

U.S. PATENT DOCUMENTS

| 5,864,039 | A | 1/1999 | Kawakita et al. |
| 2003/0207875 | A1 | 11/2003 | Gymer et al. |
| 2004/0127514 | A1 | 7/2004 | Katsu et al. |
| 2005/0148573 | A1 | 7/2005 | Katsu et al. |
| 2005/0277671 | A1 | 12/2005 | Ando et al. |
| 2006/0194842 | A1 | 8/2006 | Uchida et al. |
| 2008/0255113 | A1 | 10/2008 | Kato et al. |
| 2008/0293767 | A1 | 11/2008 | Kato et al. |

FOREIGN PATENT DOCUMENTS

| JP | 2003-212868 | A | 7/2003 | |
| JP | 2007-533613 | | 11/2005 | |
| JP | 2006-502180 | A | 1/2006 | |
| JP | 2007-512313 | A | 5/2007 | |
| JP | 2007-519708 | A | 7/2007 | |
| JP | 2008-509088 | A | 3/2008 | |
| JP | 2008-531543 | | 8/2008 | |
| WO | WO-9711054 | A1 | 3/1997 | |
| WO | WO 2005/021539 | * | 3/2005 | ........... C07D 405/14 |
| WO | WO-2005092882 | A1 | 10/2005 | |
| WO | WO-2007096352 | A1 | 8/2007 | |

OTHER PUBLICATIONS

Bockaert et al., "5-HT4 Receptors: Potential Therapeutic Implications in Neurology and Psychiatry," *CNS Drugs* 1: 6-15, 1994.

Bockaert et al., "The 5-HT4 receptor: a place in the sun," *TiPs* 13: 141-45. 1992.

Cho et al., "Activation of 5-HT4 receptors inhibits secretion of β-amyloid peptides and increases neuronal survival," *Experimental Neurology* 203: 274-278, 2007.

Eglen et al., "Central 5-HT4 receptors," *TiPs* 16: 391-398, 1995.

Ford et al.,"The 5-HT4 Receptor," *Med. Res. Rev.* 13: 633-62, 1993.

Francis et al., "The cholinergic hypothesis of Alzheimer's disease: a reivew of progress," *J Neurol Neruosurg Psychiatry* 66: 137-147, 1999.

Gong et al., "Alzheimer's disease-affected brain: Presence of oligomeric Aβ ligands (ADDLs) suggests a molecular basis for reversible memory loss," *PNAS* 100: 10417-10422, 2003.

(Continued)

*Primary Examiner* — Alicia L Otton (74) *Attorney, Agent, or Firm* — Marshall, Gerstein & Borun LLP (57) ABSTRACT

This invention relates to a compound of formula (I) or a pharmaceutically acceptable salt thereof with 5-HT4 agonistic activities, which is useful in the treatment of dementia. This invention also relates to a pharmaceutical composition for the treatment of dementia which comprises a therapeutically effective amount of a compound of formula (I) or a pharmaceutically acceptable salt thereof. Further this invention relates to a method for the treatment of dementia in an animal subject including a mammalian subject, which comprises administering to the animal subject including a mammalian subject a compound of the formula (I) or a pharmaceutically acceptable salt thereof.

(I)

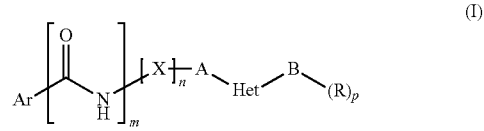

3 Claims, 1 Drawing Sheet

(56) References Cited

OTHER PUBLICATIONS

Gullickson et al., "Gastrointestinal Motility Responses to the S and R Enantiomers of Zacopride, a 5-HT4 Agonist and 5-HT3 Antagonist," *Drug Dev. Res.* 26: 405-17, 1992.

Hardy et al., "The Amyloid Hypothesis of Alzheimer's Disease: Progress and Problems on the Road to Therapeutics," *Science* 297: 353-356, 2002.

International Search Report in corresponding PCT/JP2011/000793 dated Apr. 26, 2011.

Kaumann et al., "A 5-HT4-like receptor in human right atrium," *Naunyn-Schmiedebergs Arch. Pharmacol.* 344: 150-159, 1991.

Mount et al., "Alzheimer's disease: progress or profit?" *Nature Medicine* 12: 780-784, 2006.

Romanelli et al., "Synthesis and Biological Activity of a Series of Aryl Tropanyl Esters and Amides Chemically related to 1H-Indole-3-carboxylic Acid endo 8-Methyl-8-azabicyclo[3/2/1]oct030yl Ester," *Arzheim Forsch./Drug Res.*, 43:913-918, 1993.

Shacham et al., "PRX-03140: A Novel 5-HT4 Partial Agonist with a Dual Cholinergic/Disease-Modifying Mechanism for the Treatment fo Alzheimer Disease," *10th ICAD* Mar. 5, 2003, 2006.

Siemers et al., "Safety, Tolerability, and Effects on Plasma and Cerbrospinal Fluid Amyloid-$\beta$ After Inhibition of $\gamma$-Secretase," *Clinical Neuropharmacology* 30: 317-325, 2007.

Written Opinion in corresponding PCT/JP2011/000793 dated Apr. 26, 2011.

\* cited by examiner

5-HT4 RECEPTOR AGONISTS FOR THE TREATMENT OF DEMENTIA

TECHNICAL FIELD

This invention relates to compounds for use in therapeutic treatment of the human body. In particular, it relates to compounds with selective 5-HT4 receptor agonism which are useful for treating dementia, or preventing or delaying the onset or the progression of dementia that is associated with the augmentation of beta-amyloid peptide (Abeta) in the brain, and/or associated with a depletion of ACh levels in the brain synapses.

This invention also relates to a pharmaceutical composition for the treatment of dementia which comprises a therapeutically effective amount of a compound of formula (I) or a pharmaceutically acceptable salt thereof. This invention relates to a method for the treatment of dementia in an animal subject including a mammalian subject, which comprises administering to the animal subject including a mammalian subject a compound of the formula (I) or a pharmaceutically acceptable salt thereof. Further this invention relates to a method for the treatment of dementia in an animal subject including a mammalian subject, which comprises administering to the animal subject including a mammalian subject in need a therapeutically effective amount of a compound of the formula (I) or a pharmaceutically acceptable salt thereof.

BACKGROUND ART

In general, 5-HT4 receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease (AD), cognitive disorder, emesis, migraine, neurological disease, pain, cardiovascular disorders such as cardiac failure and heart arrhythmia, and apnea syndrome (See NPL 1; NPL 2; NPL 3; NPL 4; NPL 5; NPL 6; and NPL 7).

Alzheimer's disease is the most prevalent form of dementia. Its diagnosis is described in the Diagnostic and Statistical Manual of Mental Disorders, 4th ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. In the past, cholinergic hypothesis, Abeta hypothesis and tau hypothesis has been advocated and tremendous amount of researches are undertaken in each story to identify the causative mechanisms of AD.

Over the 20 years since the origins of the cholinergic hypothesis, data from numerous studies have challenged its veracity as an explanation for the syndrome of dementia in Alzheimer's disease (NPL 8). These studies, together with the emerging role of acetylcholine (ACh) in learning and memory, led to the "cholinergic hypothesis of Alzheimer's disease". Thus it was proposed that degeneration of cholinergic neurons in the basal forebrain and the associated loss of cholinergic neurotransmission in the cerebral cortex and other areas contributed significantly to the deterioration of cognitive function seen in patients with AD. Based on this mechanism of action, acetylcholine esterase inhibitors which suppress the degradation of acetylcholine in brain synapses are in the market as the therapeutic medicines for AD.

Abeta is formed from amyloid precursor protein (APP) via separate intracellular proteolytic events involving the enzymes beta-secretase and gamma-secretase. Variability in the site of the proteolysis mediated by gamma-secretase results in Abeta of varying chain length, e.g. Abeta(1-38), Abeta(1-40) and Abeta(1-42). After secretion into the extracellular medium, Abeta forms initially-soluble aggregates which are widely believed to be the key neurotoxic agents in AD (see NPL 9), and which ultimately result in the insoluble deposits and dense neuritic plaques which are the pathological characteristics of AD (NPL 10). Several candidates of AD therapeutics based on this hypothesis, are presently in the clinical trials and some efficacy in AD patients were reported (NPL 11, NPL 12).

Above two mechanisms, 1) the induction of acetylcholine levels in the brain, and 2) the suppression of Abeta production following deposition of amyloid plaques in the cortical and associative brain regions are the promising mechanisms for AD therapy proofed in human. The mechanism 1) is exemplified by acetylcholine esterase inhibitors such as donepezil, galantamine, and rivastigmine, in the market, and the mechanism 2) is exemplified by the drugs such as Abeta antibody and secretase inhibitors, and their efficacy has been reported in clinical studies of AD.

These two mechanisms are expected to show different efficacy on the AD therapy. The mechanism 1) restores the memory and cognitive functions in patients while it is a symptomatic therapy. In the other hand, the mechanism 2) by the suppression of Abeta production should have neuro-protective function which brings a disease-modifying therapy in AD patients. Therefore, a medicine which has both mechanisms of action will be an attractive medicine for AD therapy. As far as we know, this invention is the first example of the compound which has been demonstrated both mechanisms 1) and 2) clearly in animals.

Particularly in AD, it is discussed in the literatures that 5-HT4 agonism provides both the proposed mechanisms of treatment mentioned above. Then some 5-HT4 agonists have been synthesized and the non-clinical and clinical studies have been commenced by using the agonists. However, no effective working examples in animal Abeta reducing study have been identified. For example, PRX-03140, which is developed in clinical stage, has showed Abeta reducing tendency while those efficacies were not significant suppressions in animal models (NPL 13). RS67333 has been tested for the inhibition of Abeta secretion using cell culture but has not been tested in animals (NPL 14). Therefore, this invention is the first example of the compound which has been demonstrated both above two mechanisms clearly in animals.

CITATION LIST

Non Patent Literature

NPL 1: Bockaert J. et al., TiPs 13; 141-45, 1992
NPL 2: Ford A. P et al., Med. Res. Rev. 13: 633-62, 1993
NPL 3: Gullikson G. W. et al., Drug Dev. Res. 26; 405-17, 1992
NPL 4: Richard M. Eglen et al., TiPs 16; 391-98, 1995
NPL 5: Bockaert J. et al., CNS Drugs 1; 6-15, 1994
NPL 6: Romanelli M. N. et al., Arzheim Forsch./Drug Res., 43; 913-18, 1993
NPL 7: Kaumann A. J. et al., Naunyn-Schmiedebergs Arch Pharmacol., 344; 150-59, 1991
NPL 8: Francis P et al., J Neurol Neurosurg Psychiatry 66; 137-147, 1999
NPL 9: Gong Y et al., PNAS 100; 10417-22, 2003

NPL 10: Hardy J et al., Science 297; 353-356, 2002
NPL 11: Mount C et al., Nature Medicine 12; 780-784, 2006
NPL 12: Siemers E R et al., Clinical Neuropharmacology 30; 317-325, 2007
NPL 13: Shacham S et al., 10th ICAD O3-05-03, 2006
NPL 14: Cho, S et al., Experimental Neurology 203; 274-278, 2007

SUMMARY OF INVENTION

Technical Problem

An object of the present invention is to provide compounds for use in therapeutic treatment of the human body. In particular, an object of the present invention is to provide compounds with selective 5-HT4 receptor agonism which are useful for treating dementia, or preventing or delaying the onset or the progression of dementia that is associated with the augmentation of Abeta in the brain, and/or associated with a depletion of ACh levels in the brain synapses.

In addition, an object of the present invention is to provide a pharmaceutical composition for the treatment of dementia which comprises a therapeutically effective amount of a compound of formula (I) or a pharmaceutically acceptable salt thereof, a method for the treatment of dementia in an animal subject including a mammalian subject, which comprises administering to the animal subject including a mammalian subject a compound of the formula (I) or a pharmaceutically acceptable salt thereof, and a method for the treatment of dementia in an animal subject including a mammalian subject, which comprises administering to the animal subject including a mammalian subject in need a therapeutically effective amount of a compound of the formula (I) or a pharmaceutically acceptable salt thereof.

Solution to Problem

The gist of the present invention is as follows:

[1] Use of a compound of the formula (I) or a pharmaceutically acceptable salt thereof in the manufacture of a medicament for the treatment of dementia in an animal subject including a mammalian subject:

[Chem.1]

$$Ar \underset{H}{\overset{O}{\underset{\|}{C}}} \underset{m}{N} {\left[ X \right]_n} A \underset{Het}{\diagup} B \diagdown (R)_p \quad (I)$$

wherein

Het represents a heterocyclic group having one nitrogen atom and from 4 to 7 carbon atoms, to which B binds directly, said heterocyclic group being unsubstituted or substituted by 1 to 4 substituents independently selected from the group consisting of substituents alpha$^1$;

said substituents alpha$^1$ are independently selected from a hydroxy group, a halogen atom and an amino group;

A represents an alkylene group having from 1 to 4 carbon atoms;

B represents a covalent bond or an alkylene group having from 1 to 5 carbon atoms;

Ar represents aryl which may be optionally substituted with 1 to 5 substituents independently selected from the group consisting of hydrogen, halogen, $C_1$-$C_4$ alkyl, $C_4$-$C_6$ cycloalkyl, —O—$C_1$-$C_4$ alkyl, —O-heterocyclyl and —O—$CH_2$—$R^2$; wherein said $C_4$-$C_6$ cycloalkyl is unsubstituted or substituted with 1 to 4 substituents independently selected from the group consisting of hydroxy, oxo and $C_1$-$C_4$ alkoxy;

$R^2$ is selected from the group consisting of trifluoromethyl, isopropyl and $C_4$-$C_6$ cycloalkyl; wherein said $C_4$-$C_6$ cycloalkyl is unsubstituted or substituted with 1 to 4 substituents independently selected from the group consisting of hydroxy, oxo, $C_1$-$C_4$ alkoxy and hydroxy-$C_1$-$C_4$ alkyl;

X represents —O—, —S—, —NH—, or —$CH_2$— n represents 0 or 1;

m represents 0 or 1;

R independently represents (i) an oxo group, a hydroxy group, an amino group, an alkylamino group, a carboxyl group or a tetrazole group;

(ii) a cycloalkyl group having from 3 to 8 carbon atoms, said cycloalkyl group being substituted by 1 to 5 substituents independently selected from the group consisting of substituents alpha$^2$, or (iii) a heterocyclic group having from 3 to 8 atoms, said heterocyclic group being unsubstituted or substituted by 1 to 5 substituents independently selected from the group consisting of substituents beta, said substituents alpha$^2$ are independently selected from a hydroxy group, an amino group, a hydroxy-substituted alkyl group having from 1 to 4 carbon atoms, a carboxyl group, an alkoxy group having from 1 to 4 carbon atoms, and a tetrazole group;

said substituents beta are independently selected from a hydroxy group, a hydroxy-substituted alkyl group having from 1 to 4 carbon atoms, a carboxyl group, an amino group, an alkyl group having from 1 to 4 carbon atoms, an amino-substituted alkyl group having from 1 to 4 carbon atoms, a carbamoyl group, and a tetrazole group; and p represents 1, 2 or 3;

[2] The use of [1], wherein

Het represents a heterocyclic group selected from

[Chem.2]

said heterocyclic group being unsubstituted or substituted by 1 to 4 substituents independently selected from the group consisting of substituents alpha$^1$;

said substituents alpha$^1$ are independently selected from a hydroxy group, and a halogen atom;

A represents an alkylene group having from 1 to 2 carbon atoms;

B represents an alkylene group having from 1 to 5 carbon atoms;

Ar represents,

[Chem.3]

$R^{1a}$ represents an isopropyl group, an n-propyl group or a cyclopentyl group, $R^{2a}$ represents a methyl group, a fluorine atom or a chlorine atom;

[Chem.4]

$R^{1b}$ represents an alkyl group having from 1 to 4 carbon atoms or a halogen atom, $R^{2b}$ represents an alkyl group having from 1 to 4 carbon atoms;

[Chem.5]

$R^{1c}$ is selected from the group consisting of $C_4$-$C_6$ cycloalkyl, heterocyclyl and —$CH_2$—$R^{2c}$; wherein said $C_4$-$C_6$ cycloalkyl is unsubstituted or substituted with 1 to 4 substituents independently selected from the group consisting of hydroxy, oxo and $C_1$-$C_4$ alkoxy;

$R^{2c}$ is selected from the group consisting of trifluoromethyl, isopropyl and $C_4$-$C_6$ cycloalkyl; wherein said $C_4$-$C_6$ cycloalkyl is unsubstituted or substituted with 1 to 4 substituents independently selected from the group consisting of hydroxy, oxo, $C_1$-$C_4$ alkoxy and hydroxy-$C_1$-$C_4$ alkyl;

[Chem.6]

$R^{1d}$ is a hydrogen atom, a halogen atom or a $C_1$-$C_6$ alkyl group;

$R^{2d}$ is a $C_1$-$C_6$ alkyl group or a $C_3$-$C_6$ cycloalkyl group;

[Chem.7]

$R^{1e}$ represents an isopropyl group or a cyclopentyl group;

$R^{2e}$ independently represents a halogen atom or an alkyl group having from 1 to 4 carbon atoms; q is 0, 1, 2, 3 or 4;

[Chem.8]

$R^{1f}$ represents a hydrogen atom, a halogen atom or a $C_1$-$C_4$ alkyl group;

$R^{2f}$ and $R^{3f}$ represent independently a methyl or ethyl group, or $R^{2f}$ and $R^{3f}$ may together form a $C_2$-$C_4$ alkylene bridge to yield a 3 to 5 membered ring;

[Chem.9]

$R^{1g}$ represents a $C_1$-$C_4$ alkyl group, a —$CH_2$—$C_3$-$C_6$-cycloalkyl group or $C_3$-$C_6$-cycloalkyl group;

$R^{2g}$ represents a hydrogen atom or a halogen atom;

[Chem.10]

$R^{1h}$ represents a $C_1$-$C_4$ alkyl group;

$R^{2h}$ represents a hydrogen atom or a halogen atom;

q represents 1 or 2;

[Chem.11]

[Chem.12]

$R^{1i}$ represents a $C_1$-$C_4$ alkyl group;
$R^{2i}$ represents a hydrogen atom or a halogen atom;
r represents 1 or 2;

[Chem.13]

$R^{1j}$ represents a $C_1$-$C_4$ alkyl group;
$R^{2j}$ represents a hydrogen atom or a halogen atom; or

[Chem.14]

X represents —O— when Ar represents

[Chem.15]

n represents 1 when Ar represents

[Chem.16]

m represents 0 or 1;
R independently represents
(i) a hydroxy group, an amino group, an alkylamino group, or a carboxyl group;
(ii) a cycloalkyl group having from 4 to 7 carbon atoms, said cycloalkyl group being substituted by 1 to 3 substituents independently selected from the group consisting of substituents alpha$^2$, or
(iii) a heterocyclic group having from 5 to 7 atoms, said heterocyclic group being unsubstituted or substituted by 1 to 3 substituents independently selected from the group consisting of substituents beta,
said substituents alpha$^2$ are independently selected from a hydroxy group, a carboxyl group, an alkoxy group having from 1 to 4 carbon atoms and a tetrazole group;
said substituents beta are independently selected from a hydroxy group, a carboxyl group, an alkyl group having from 1 to 4 carbon atoms, a carbamoyl group, and a tetrazole group;
p represents 1;
[3] The use of [2], wherein
Het represents a group of formula

[Chem.17]

and this group is unsubstituted or substituted by one substituent selected from the group consisting of substituents alpha$^1$;
said substituents alpha$^1$ are independently selected from a hydroxy group;
A represents a methylene group;
B represents a methylene group;
m represents 0 when Ar represents

[Chem.18]

R independently represents
(i) a hydroxy group;
(ii) a cycloalkyl group having from 4 to 6 carbon atoms, said cycloalkyl group being substituted by 1 to 2 substituents independently selected from the group consisting of substituents alpha$^2$, or
(iii) a heterocyclic group having from 5 to 6 atoms, said heterocyclic group being unsubstituted or substituted by 1 to 2 substituents independently selected from the group consisting of substituents beta, said substituents alpha² are independently selected from a hydroxy group, a carboxyl group, and a tetrazole group;

said substituents beta are selected from a hydroxy group, a carboxyl group, an alkyl group having from 1 to 4 carbon atoms, and a tetrazole group;

p represents 1;

[4] The use of [3], wherein

R independently represents a 1,4-dihydroxycyclohexyl group, a hydroxycyclopentyl group, a hydroxytetrahydropyranyl group, a tetrazolyltetrahydropyranyl group, a tetrazolylcyclopentyl group, a piperidinyl group or a morpholinyl group;

[5] The use of [1], wherein the compound of formula (I) is selected from:

N-((1-((1-(2H-Tetrazol-5-yl)cyclopentyl)methyl)piperidin-4-yl)methyl)-3-isopropyl-2-oxo-2,3-dihydro-1H-benzo[d]imidazole-1-carboxamide;

3-isopropyl-N-((1-(2-Methyl-2-(2H-tetrazol-5-yl)propyl)piperidin-4-yl)methyl)-2-oxo-2,3-dihydro-1H-benzo[d]imidazole-1-carboxamide;

N-((1-((1-(2H-Tetrazol-5-yl)cyclopentyl)methyl)piperidin-4-yl)methyl)-2'-oxospiro[cyclopentane-1,3'-indoline]-1'-carboxamide;

N-((1-(((4-hydroxytetrahydro-2H-pyran-4-yl)methyl)piperidin-4-yl)methyl)-3-isopropyl-2-oxo-2,3-dihydro-1H-benzo[d]imidazole-1-carboxamide;

5-Fluoro-N-((1-((4-hydroxytetrahydro-2H-pyran-4-yl)methyl)piperidin-4-yl)methyl)-1-isopropyl-2-oxo-1,2-dihydroquinoline-3-carboxamide;

5-Chloro-N-((1-(((4-hydroxytetrahydro-2H-pyran-4-yl)methyl)piperidin-4-yl)methyl)-1-isopropyl-2-oxo-1,2-dihydroquinoline-3-carboxamide;

N-((1-(((4-Hydroxytetrahydro-2H-pyran-4-yl)methyl)piperidin-4-yl)methyl)-1-isopropyl-5-methyl-2-oxo-1,2-dihydroquinoline-3-carboxamide;

N-((1-((trans-1,4-Dihydroxycyclohexyl)methyl)piperidin-4-yl)methyl)-1-isopropyl-5-methyl-2-oxo-1,2-dihydroquinoline-3-carboxamide;

N-((1-((cis-1,4-Dihydroxycyclohexyl)methyl)piperidin-4-yl)methyl)-1-isopropyl-5-methyl-2-oxo-1,2-dihydroquinoline-3-carboxamide;

5-Bromo-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide oxalate;

5-Chloro-N-((1-(((trans-1,4-dihydroxy-4-methylcyclohexyl)methyl)piperidin-4-yl)methyl)-1-isopropyl-6-methyl-2-oxo-1,2-dihydropyridine-3-carboxamide;

5-Chloro-N-((1-(((trans-1-hydroxy-4-methoxycyclohexyl)methyl)piperidin-4-yl)methyl)-1-isopropyl-6-methyl-2-oxo-1,2-dihydropyridine-3-carboxamide;

5-Chloro-N-((1-(((cis-1-hydroxy-4-methoxycyclohexyl)methyl)piperidin-4-yl)methyl)-1-isopropyl-6-methyl-2-oxo-1,2-dihydropyridine-3-carboxamide;

5-Chloro-N-((1-(((1-hydroxycyclohexyl)methyl)piperidin-4-yl)methyl)-1-isopropyl-6-methyl-2-oxo-1,2-dihydropyridine-3-carboxamide;

5-Chloro-N-((1-(cyclohexylmethyl)piperidin-4-yl)methyl)-1-isopropyl-6-methyl-2-oxo-1,2-dihydropyridine-3-carboxamide;

5-Fluoro-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide;

5-Bromo-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide;

N-((1-(((4-Hydroxytetrahydro-2H-pyran-4-yl)methyl)piperidin-4-yl)methyl)-1-isopropyl-5,6-dimethyl-2-oxo-1,2-dihydropyridine-3-carboxamide;

5-Chloro-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide;

4-((4-(((4-((trans-4-Hydroxycyclohexyl)oxy)benzo[d]isoxazol-3-yl)oxy)methyl)piperidin-1-yl)methyl)tetrahydro-2H-pyran-4-ol;

4-((4-(((4-(((1S,2R)-2-Hydroxycyclohexyl)oxy)benzo[d]isoxazol-3-yl)oxy)methyl)piperidin-1-yl)methyl)tetrahydro-2H-pyran-4-ol;

4-((4-(((4-(((1R,3R)-3-Hydroxycyclopentyl)oxy)benzo[d]isoxazol-3-yl)oxy)methyl)piperidin-1-yl)methyl)tetrahydro-2H-pyran-4-ol;

4-((4-(((4-(((1S,2R)-2-Methoxycyclopentyl)oxy)benzo[d]isoxazol-3-yl)oxy)methyl)piperidin-1-yl)methyl)tetrahydro-2H-pyran-4-ol;

4-((4-(((4-(((1S,2R)-2-Hydroxycyclopentyl)oxy)benzo[d]isoxazol-3-yl)oxy)methyl)piperidin-1-yl)methyl)tetrahydro-2H-pyran-4-ol;

4-((4-(((4-(((1R,2R)-2-Methoxycyclopentyl)oxy)benzo[d]isoxazol-3-yl)oxy)methyl)piperidin-1-yl)methyl)tetrahydro-2H-pyran-4-ol;

4-((4-(((4-(((1R,2R)-2-Hydroxycyclopentyl)oxy)benzo[d]isoxazol-3-yl)oxy)methyl)piperidin-1-yl)methyl)tetrahydro-2H-pyran-4-ol;

4-((4-(((4-((1-Hydroxycyclopentyl)methoxy)benzo[d]isoxazol-3-yl)oxy)methyl)piperidin-1-yl)methyl)tetrahydro-2H-pyran-4-ol;

4-((4-(((4-(Tetrahydro-2H-pyran-4-yl)oxy)benzo[d]isoxazol-3-yl)oxy)methyl)piperidin-1-yl)methyl)tetrahydro-2H-pyran-4-ol;

4-((4-(((4-Isobutoxybenzo[d]isoxazol-3-yl)oxy)methyl)piperidin-1-yl)methyl)tetrahydro-2H-pyran-4-ol;

N-(cis-6-(((4-Hydroxytetrahydro-2H-pyran-4-yl)methyl)piperidin-3-yl)-1-isopropyl-1H-indazole-3-carboxamide;

N-(cis-6-(2-Hydroxy-2-methylpropyl)piperidin-3-yl)-1-isopropyl-1H-indazole-3-carboxamide;

1-Cyclobutyl-N-(cis-6-[(4-hydroxytetrahydro-2H-pyran-4-yl)methyl]piperidin-3-yl)-1H-indazole-3-carboxamide;

N-((3S,5S)-5-(2-Hydroxy-2-methylpropyl)pyrrolidin-3-yl)-1-isopropyl-1H-indazole-3-carboxamide;

5-Fluoro-N-((3S,5S)-5-(2-hydroxy-2-methylpropyl)pyrrolidin-3-yl)-1-isopropyl-1H-indazole-3-carboxamide;

N-((3S,5S)-5-[(1-Hydroxycyclohexyl)methyl]pyrrolidin-3-yl)-1-isopropyl-1H-indazole-3-carboxamide;

4-Amino-5-chloro-N-((1-((1,4-dihydroxycyclohexyl)methyl)piperidin-4-yl)methyl)-2,3-dihydrobenzofuran-7-carboxamide;

4-Amino-5-chloro-N-((1-((4-hydroxytetrahydro-2H-pyran-4-yl)methyl)piperidin-4-yl)methyl)-2,3-dihydrobenzofuran-7-carboxamide;

4-Amino-5-chloro-N-((1-((1,4-dihydroxycyclohexyl)methyl)piperidin-4-yl)methyl)-2-ethoxybenzamide;

4-Amino-5-chloro-2-ethoxy-N-((1-((4-hydroxytetrahydro-2H-pyran-4-yl)methyl)piperidin-4-yl)methyl)benzamide;

4-Amino-5-chloro-N-((1-((1,4-dihydroxycyclohexyl)methyl)piperidin-4-yl)methyl)-2-methoxybenzamide;

4-Amino-5-chloro-N-((1-((4-hydroxytetrahydro-2H-pyran-4-yl)methyl)piperidin-4-yl)methyl)-2-methoxybenzamide;

5-Amino-6-bromo-N-((1-(((tetrahydro-2H-pyran-4-yl)methyl)piperidin-4-yl)methyl)chroman-8-carboxamide;

4-Amino-5-chloro-N-((1-(((tetrahydrofuran-2-yl)methyl)piperidin-4-yl)methyl)benzofuran-7-carboxamide;

8-Amino-7-chloro-N-((1-((tetrahydrofuran-2-yl)methyl)piperidin-4-yl)methyl)-2,3-dihydrobenzo[b][1,4]dioxine-5-carboxamide;
(S)-5-Amino-6-chloro-N-((1-((tetrahydrofuran-2-yl)methyl)piperidin-4-yl)methyl)chroman-8-carboxamide;
(S)-4-Amino-5-chloro-2-methoxy-N-((1-((tetrahydrofuran-2-yl)methyl)piperidin-4-yl)methyl)benzamide;
(R)-4-Amino-5-chloro-2-methoxy-N-((1-((tetrahydrofuran-2-yl)methyl)piperidin-4-yl)methyl)benzamide;
(S)-4-Amino-5-chloro-N-((1-((tetrahydrofuran-2-yl)methyl)piperidin-4-yl)methyl)benzofuran-7-carboxamide;
(R)-4-Amino-5-chloro-N-((1-((tetrahydrofuran-2-yl)methyl)piperidin-4-yl)methyl)benzofuran-7-carboxamide;
(S)-5-Amino-6-chloro-N-((1-((tetrahydrofuran-3-yl)methyl)piperidin-4-yl)methyl)chroman-8-carboxamide;
(R)-5-Amino-6-chloro-N-((1-((tetrahydrofuran-3-yl)methyl)piperidin-4-yl)methyl)chroman-8-carboxamide;
(S)-8-Amino-7-chloro-N-((1-((tetrahydrofuran-2-yl)methyl)piperidin-4-yl)methyl)-2,3-dihydrobenzo[b][1,4]dioxine-5-carboxamide;
(R)-8-Amino-7-chloro-N-((1-((tetrahydrofuran-2-yl)methyl)piperidin-4-yl)methyl)-2,3-dihydrobenzo[b][1,4]dioxine-5-carboxamide; and
4-Amino-5-chloro-N-((1-((tetrahydro-2H-pyran-4-yl)methyl)piperidin-4-yl)methyl)benzofuran-7-carboxamide,
or a pharmaceutically acceptable salt thereof;

[6] The use of [1], wherein the compound of the formula (I) or the pharmaceutically acceptable salt is used in combination with one or more additional compounds known to be useful in the treatment or prevention of dementia or the symptoms thereof;

[7] A pharmaceutical composition for the treatment of dementia which comprises a therapeutically effective amount of a compound of the formula (I) in claim 1 or a pharmaceutically acceptable salt thereof;

[8] The pharmaceutical composition of [7], which further comprises a therapeutically effective amount of one or more additional compounds known to be useful in the treatment or prevention of dementia or the symptoms thereof;

[9] A method for the treatment of dementia in an animal subject including a mammalian subject, which comprises administering to the animal subject including a mammalian subject a compound of the formula (I) in [1] or a pharmaceutically acceptable salt thereof;

[10] The method of [9], which further comprises administering a therapeutically effective amount of one or more additional compounds known to be useful in the treatment or prevention of dementia;

[11] A method for the treatment of dementia, which comprises administering to an animal subject including a mammalian subject in need a therapeutically effective amount of a compound of the formula (I) in [1] or a pharmaceutically acceptable salt thereof;

[12] The method of [11], which further comprises administering a therapeutically effective amount of one or more additional compounds known to be useful in the treatment or prevention of dementia; and

[13] A compound of the formula (I) in [1] or a pharmaceutically acceptable salt thereof for use in the treatment of dementia in an animal subject including a mammalian subject.

Advantageous Effects of Invention

It has now surprisingly been found that compounds of this invention which have a strong affinity to 5-HT4 receptor are useful for the treatment of dementia.

Namely, inventors confirmed that above compounds of this invention have the desirable property for the treatment of AD using the rat Novel Object Recognition Test and rat scopolamine-induced spontaneous alteration model, based on the mechanism 1) mentioned above. Compounds of this invention have also been confirmed to have the desirable property for the treatment of AD using quantitating Abeta-peptides in the Tg2576 mice, based on the mechanism 2) mentioned above.

Therefore the compounds of this invention are useful for the treatment of dementia.

DESCRIPTION OF EMBODIMENTS

The compounds of this invention for the treatment of dementia are the following formula (I):

[Chem.19]

wherein
Het represents a heterocyclic group having one nitrogen atom and from 4 to 7 carbon atoms, to which B binds directly, said heterocyclic group being unsubstituted or substituted by 1 to 4 substituents independently selected from the group consisting of substituents alpha$^1$;
said substituents alpha$^1$ are independently selected from a hydroxy group, a halogen atom and an amino group;
A represents an alkylene group having from 1 to 4 carbon atoms;
B represents a covalent bond or an alkylene group having from 1 to 5 carbon atoms;
Ar represents aryl which may be optionally substituted with 1 to 5 substituents independently selected from the group consisting of
hydrogen, halogen, $C_1$-$C_4$ alkyl, $C_4$-$C_6$ cycloalkyl, —O—$C_1$-$C_4$ alkyl, —O-heterocyclyl and —O—$CH_2$—$R^2$;
wherein said $C_4$-$C_6$ cycloalkyl is unsubstituted or substituted with 1 to 4 substituents independently selected from the group consisting of hydroxy, oxo and $C_1$-$C_4$ alkoxy;
$R^2$ is selected from the group consisting of trifluoromethyl, isopropyl and $C_4$-$C_6$ cycloalkyl; wherein said $C_4$-$C_6$ cycloalkyl is unsubstituted or substituted with 1 to 4 substituents independently selected from the group consisting of hydroxy, oxo, $C_1$-$C_4$ alkoxy and hydroxy-$C_1$-$C_4$ alkyl;
X represents —O, S, NH, or —$CH_2$—
n represents 0 or 1;
m represents 0 or 1;
R independently represents
(i) an oxo group, a hydroxy group, an amino group, an alkylamino group, a carboxyl group or a tetrazole group;

(ii) a cycloalkyl group having from 3 to 8 carbon atoms, said cycloalkyl group being substituted by 1 to 5 substituents independently selected from the group consisting of substituents alpha$^2$, or (iii) a heterocyclic group having from 3 to 8 atoms, said heterocyclic group being unsubstituted or substituted by 1 to 5 substituents independently selected from the group consisting of substituents beta, said substituents alpha$^2$ are independently selected from a hydroxy group, an amino group, a hydroxy-substituted alkyl group having from 1 to 4 carbon atoms, a carboxyl group, an alkoxy group having from 1 to 4 carbon atoms, and a tetrazole group;

said substituents beta are independently selected from a hydroxy group, a hydroxy-substituted alkyl group having from 1 to 4 carbon atoms, a carboxyl group, an amino group, an alkyl group having from 1 to 4 carbon atoms, an amino-substituted alkyl group having from 1 to 4 carbon atoms, a carbamoyl group, and a tetrazole group; and p represents 1, 2 or 3, or a pharmaceutically acceptable salt thereof.

The compounds of this invention include solvates, hydrates, complexes, polymorphs, prodrugs, isomers, and isotopically-labelled compounds.

Also, the present invention provides a pharmaceutical composition for the treatment of dementia in an animal subject including a mammalian subject, which comprises administering to said subject a therapeutically effective amount of a compound of formula (I) or pharmaceutically acceptable salts thereof.

Further, the present invention also provides a pharmaceutical composition for the treatment of dementia which comprises a therapeutically effective amount of the quinolonecarboxylic acid compound of formula (I) or its pharmaceutically acceptable salt together with a pharmaceutically acceptable carrier.

Also, the present invention provides a method for the treatment of dementia in an animal subject including a mammalian subject, which comprises administering to said subject in need a therapeutically effective amount of a compound of formula (I) or pharmaceutically acceptable salts thereof. Further, the present invention provides a method for the treatment of dementia in an animal subject including a mammalian subject, which comprises administering to the animal subject including a mammalian subject a compound of the formula (I) or a pharmaceutically acceptable salt thereof. Furthermore, the present invention provides use of the compound of formula (I) or pharmaceutically acceptable salts thereof in the manufacture of a medicament for the treatment of dementia in an animal subject including a mammalian subject.

The term "animal subject," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese.

The term "dementia" includes AD and other type of dementia that associate with the augmentation of Abeta-peptides and/or depletion of ACh levels in the brain, such as vascular dementia, neurodegenerative disease-associated dementia, Parkinson's disease-related dementia, frontotemporal dementia, pick complex, Diffuse Lewy body-related dementia, traumatic brain injury- or hypoxic-ischemic injury-associated dementia, depression- or schizophrenia-associated dementia, Huntington's disease-associated dementia, HIV-related dementia. The term "dementia" also includes the clinical symptoms such as cognitive dysfunction, memory loss and behavioral changes which are associated with the augmentation of Abeta-peptides and/or depletion of ACh levels in the brain in the diseases mentioned above.

As used herein, the term "heterocyclic" of "Het" means a heterocyclic group having one nitrogen atom and from 4 to 7 carbon atoms such as

[Chem.20]

and

As used herein, the term "alkylene" in "A" means straight or branched chain saturated radicals having 1 to 4 carbon atoms, including, but not limited to methylene, ethylene, n-propylene, isopropylene, n-butylene, isobutylene, sec-butylene, tert-butylene and the like. The "alkylene" in "A" represents preferably a methylene group, an ethylene group or a propylene group; more preferably a methylene group or an ethylene group; most preferably a methylene group.

As used herein, the term "alkylene" in "B" means straight or branched chain saturated radicals having 1 to 5 carbon atoms, including, but not limited to methylene, ethylene, n-propylene, isopropylene, n-butylene, isobutylene, sec-butylene, tert-butylene, n-pentylene, isopentylene, sec-pentylene, tert-pentylene and the like. The "alkylene" in "B" represents preferably an alkylene group having from 1 to 4 carbon atoms; more preferably an alkylene group having from 1 to 3 carbon atoms; much more preferably a methylene group or an ethylene group; further more preferably a methylene group.

As used herein, the term "alkyl" of "an alkylamino" in "R"; "alkyl" of "a hydroxy-substituted alkyl group" and "an alkoxy group having from 1 to 4 carbon atoms" in "substituents alpha$^2$"; "alkyl" in "substituents beta"; and "alkyl" of "a hydroxy-substituted alkyl group" and "an amino-substituted alkyl group" in "substituents beta" mean straight or branched chain saturated radicals having 1 to 4 carbon atoms, including, but not limited to methyl, ethyl, n-propyl, isopropyl, n-butyl, isobutyl, secbutyl, tert-butyl and the like.

As used herein, the term "cycloalkyl" in "R" means a cyclic alkyl group having 3 to 8 carbon atoms, such as cyclopropyl, cyclobutyl, cyclopentyl, cyclohexyl, cycloheptyl, cyclooctyl, and the like.

As used herein, the term "heterocyclic" of "R" means a heterocyclic ring which has one or more heteroatoms in the ring, preferably has 2 to 6 carbon atoms and 1 to 3 heteroatoms, including aziridinyl, azetidinyl, piperidinyl, morpholinyl(including morpholino), pyrrolidinyl, pyrazolidinyl, piperazinyl, tetrahydropyrazolyl, pyrazolinyl, tetrahydropyranyl and the like.

The term "treating", as used herein, refers to reversing, alleviating, inhibiting, or preventing the onset or the progression of the disorder or condition to which such term applies, or one or more symptoms of such disorder or condition. The term "treatment" as used herein refers to the act of treating, as "treating" is defined immediately above.

The substituents "R" can be bonded at carbon atom which connects "B group" and "R group", such as formulas as follows:

[Chem.21]

Each substituent of a preferable, more preferable or most preferable compound of formula (I) is as follows:

Het represents preferably a heterocyclic group selected from

[Chem.22]

said heterocyclic group being unsubstituted or substituted by 1 to 4 substituents independently selected from the group consisting of substituents alpha$^1$;

Het represents more preferably a group of formula

[Chem.23]

this group being unsubstituted or substituted by one substituent selected from the group consisting of substituents alpha$^1$;

said substituents alpha$^1$ are independently selected preferably from a hydroxy group, and a halogen atom; said substituents alpha$^1$ are independently selected more preferably from a hydroxy group;

A represents an alkylene group having from 1 to 2 carbon atoms; more preferably A represents a methylene group;

B represents an alkylene group having from 1 to 5 carbon atoms; more preferably B represents an alkylene group having from 1 to 2 carbon atoms; most preferably B represents a methylene group;

Ar represents preferably,

[Chem.24]

$R^{1a}$ represents an isopropyl group, an n-propyl group or a cyclopentyl group, $R^{2a}$ represents a methyl group, a fluorine atom or a chlorine atom;

[Chem. 25]

$R^{1b}$ represents an alkyl group having from 1 to 4 carbon atoms or a halogen atom, $R^{2b}$ represents an alkyl group having from 1 to 4 carbon atoms;

[Chem. 26]

$R^{1c}$ is selected from the group consisting of $C_4$-$C_6$ cycloalkyl, heterocyclyl and —$CH_2$—$R^{2c}$; wherein said $C_4$-$C_6$ cycloalkyl is unsubstituted or substituted with 1 to 4 substituents independently selected from the group consisting of hydroxy, oxo and $C_1$-$C_4$ alkoxy;

$R^{2c}$ is selected from the group consisting of trifluoromethyl, isopropyl and $C_4$-$C_6$ cycloalkyl; wherein said $C_4$-$C_6$ cycloalkyl is unsubstituted or substituted with 1 to 4 substituents independently selected from the group consisting of hydroxy, oxo, $C_1$-$C_4$ alkoxy and hydroxy-$C_1$-$C_4$ alkyl;

[Chem. 27]

$R^{1d}$ is a hydrogen atom, a halogen atom or a $C_1$-$C_6$ alkyl group;

$R^{2d}$ is a $C_1$-$C_6$ alkyl group or a $C_3$-$C_6$ cycloalkyl group;

$R^{1e}$ represents an isopropyl group or a cyclopentyl group;

$R^{2e}$ independently represents a halogen atom or an alkyl group having from 1 to 4 carbon atoms; q is 0, 1, 2, 3 or 4;

$R^{1f}$ represents a hydrogen atom, a halogen atom or a $C_1$-$C_4$ alkyl group;

$R^{2f}$ and $R^{3f}$ represent independently a methyl or ethyl group, or $R^{2f}$ and $R^{3f}$ may together form a $C_2$-$C_4$ alkylene bridge to yield a 3 to 5 membered ring;

$R^{1g}$ represents a $C_1$-$C_4$ alkyl group, a —$CH_2$—$C_3$-$C_6$-cycloalkyl group or $C_3$-$C_6$-cycloalkyl;

$R^{2g}$ represents a hydrogen atom or a halogen atom;

$R^{1h}$ represents a $C_1$-$C_4$ alkyl group;

$R^{2h}$ represents a hydrogen atom or a halogen atom;

q represents 1 or 2;

$R^{1i}$ represents a $C_1$-$C_4$ alkyl group;

$R^{2i}$ represents a hydrogen atom or a halogen atom;

r represents 1 or 2;

[Chem. 34]

$R^{1j}$ represents a $C_1$-$C_4$ alkyl group;

$R^{2j}$ represents a hydrogen atom or a halogen atom; or

[Chem. 35]

X represents preferably —O— when Ar represents

[Chem. 36]

n represents preferably 1 when Ar represents

[Chem. 37]

m represents preferably 0 or 1; m represents most preferably 0 when Ar represents

[Chem. 38]

R independently represents preferably (i) a hydroxy group, an amino group, an alkylamino group, or a carboxyl group;

(ii) a cycloalkyl group having from 4 to 7 carbon atoms, said cycloalkyl group being substituted by 1 to 3 substituents independently selected from the group consisting of substituents alpha$^2$, or (iii) a heterocyclic group having from 5 to 7 atoms, said heterocyclic group being unsubstituted or substituted by 1 to 3 substituents independently selected from the group consisting of substituents beta, said substituents alpha$^2$ are independently selected preferably from a hydroxy group, a carboxyl group, an alkoxy group having from 1 to 4 carbon atoms and a tetrazole group; said substituents alpha$^2$ are independently selected more preferably from a hydroxy group, a carboxyl group, and a tetrazole group;

said substituents beta are independently selected preferably from a hydroxy group, a carboxyl group, an alkyl group having from 1 to 4 carbon atoms, a carbamoyl group, and a tetrazole group; said substituents beta are selected more preferably from a hydroxy group, a carboxyl group, an alkyl group having from 1 to 4 carbon atoms, and a tetrazole group;

p represents preferably 1;

more preferably R independently represents (i) a hydroxy group;

(ii) a cycloalkyl group having from 4 to 6 carbon atoms, said cycloalkyl group being substituted by 1 to 2 substituents independently selected from the group consisting of substituents alpha$^2$, or (iii) a heterocyclic group having from 5 to 6 atoms, said heterocyclic group being unsubstituted or substituted by 1 to 2 substituents independently selected from the group consisting of substituents beta, said substituents alpha$^2$ are independently selected from a hydroxy group, an amino group, and a tetrazole group;

said substituents beta are independently selected from a hydroxy group, an alkyl group having from 1 to 4 carbon atoms group, and a tetrazole group;

p represents preferably 1;

most preferably R independently represents a 1,4-dihydroxycyclohexyl group, a hydroxycyclopentyl group, a hydroxytetrahydropyranyl group, a tetrazolyltetrahydropyranyl group, a tetrazolylcyclopentyl group, a piperidinyl group or a morpholinyl group.

The most preferable compounds are:

N-((1-((1-(2H-Tetrazol-5-yl)cyclopentyl)methyl)piperidin-4-yl)methyl)-3-isopropyl-2-oxo-2,3-dihydro-1H-benzo[d]imidazole-1-carboxamide;

3-isopropyl-N-((1-(2-Methyl-2-(2H-tetrazol-5-yl)propyl)piperidin-4-yl)methyl)-2-oxo-2,3-dihydro-1H-benzo[d]imidazole-1-carboxamide;

N-((1-((1-(2H-Tetrazol-5-yl)cyclopentyl)methyl)piperidin-4-yl)methyl)-2'-oxospiro[cyclopentane-1,3'-indoline]-1'-carboxamide;

N-((1-(((4-hydroxytetrahydro-2H-pyran-4-yl)methyl)piperidin-4-yl)methyl)-3-isopropyl-2-oxo-2,3-dihydro-1H-benzo[d]imidazole-1-carboxamide;

5-Fluoro-N-((1-((4-hydroxytetrahydro-2H-pyran-4-yl)methyl)piperidin-4-yl)methyl)-1-isopropyl-2-oxo-1,2-dihydroquinoline-3-carboxamide;

5-Chloro-N-((1-((4-hydroxytetrahydro-2H-pyran-4-yl)methyl)piperidin-4-yl)methyl)-1-isopropyl-2-oxo-1,2-dihydroquinoline-3-carboxamide;

N-((1-(((4-Hydroxytetrahydro-2H-pyran-4-yl)methyl)piperidin-4-yl)methyl)-1-isopropyl-5-methyl-2-oxo-1,2-dihydroquinoline-3-carboxamide;

N-((1-((trans-1,4-Dihydroxycyclohexyl)methyl)piperidin-4-yl)methyl)-1-isopropyl-5-methyl-2-oxo-1,2-dihydroquinoline-3-carboxamide;

N-((1-((cis-1,4-Dihydroxycyclohexyl)methyl)piperidin-4-yl)methyl)-1-isopropyl-5-methyl-2-oxo-1,2-dihydroquinoline-3-carboxamide;

5-Bromo-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide oxalate;

5-Chloro-N-((1-((trans-1,4-dihydroxy-4-methylcyclohexyl)methyl)piperidin-4-yl)methyl)-1-isopropyl-6-methyl-2-oxo-1,2-dihydropyridine-3-carboxamide;

5-Chloro-N-((1-((trans-1-hydroxy-4-methoxycyclohexyl)methyl)piperidin-4-yl)methyl)-1-isopropyl-6-methyl-2-oxo-1,2-dihydropyridine-3-carboxamide;

5-Chloro-N-((1-((cis-1-hydroxy-4-methoxycyclohexyl)methyl)piperidin-4-yl)methyl)-1-isopropyl-6-methyl-2-oxo-1,2-dihydropyridine-3-carboxamide;

5-Chloro-N-((1-((1-hydroxycyclohexyl)methyl)piperidin-4-yl)methyl)-1-isopropyl-6-methyl-2-oxo-1,2-dihydropyridine-3-carboxamide;

5-Chloro-N-((1-(cyclohexylmethyl)piperidin-4-yl)methyl)-1-isopropyl-6-methyl-2-oxo-1,2-dihydropyridine-3-carboxamide;

5-Fluoro-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide;

5-Bromo-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide;

N-((1-(((4-Hydroxytetrahydro-2H-pyran-4-yl)methyl)piperidin-4-yl)methyl)-1-isopropyl-5,6-dimethyl-2-oxo-1,2-dihydropyridine-3-carboxamide;

5-Chloro-N-((1-((4-hydroxytetrahydro-2H-pyran-4-yl)methyl)piperidin-4-yl)methyl)-1-isopropyl-6-methyl-2-oxo-1,2-dihydropyridine-3-carboxamide;

4-((4-(((4-((trans-4-Hydroxycyclohexyl)oxy)benzo[d]isoxazol-3-yl)oxy)methyl)piperidin-1-yl)methyl)tetrahydro-2H-pyran-4-ol;

4-((4-(((4-(((1S,2R)-2-Hydroxycyclohexyl)oxy)benzo[d]isoxazol-3-yl)oxy)methyl)piperidin-1-yl)methyl)tetrahydro-2H-pyran-4-ol;

4-((4-(((4-(((1R,3R)-3-Hydroxycyclopentyl)oxy)benzo[d]isoxazol-3-yl)oxy)methyl)piperidin-1-yl)methyl)tetrahydro-2H-pyran-4-ol;
4-((4-(((4-(((1S,2R)-2-Methoxycyclopentyl)oxy)benzo[d]isoxazol-3-yl)oxy)methyl)piperidin-1-yl)methyl)tetrahydro-2H-pyran-4-ol;
4-((4-(((4-(((1S,2R)-2-Hydroxycyclopentyl)oxy)benzo[d]isoxazol-3-yl)oxy)methyl)piperidin-1-yl)methyl)tetrahydro-2H-pyran-4-ol;
4-((4-(((4-(((1R,2R)-2-Methoxycyclopentyl)oxy)benzo[d]isoxazol-3-yl)oxy)methyl)piperidin-1-yl)methyl)tetrahydro-2H-pyran-4-ol;
4-((4-(((4-(((1R,2R)-2-Hydroxycyclopentyl)oxy)benzo[d]isoxazol-3-yl)oxy)methyl)piperidin-1-yl)methyl)tetrahydro-2H-pyran-4-ol;
4-((4-(((4-((1-Hydroxycyclopentyl)methoxy)benzo[d]isoxazol-3-yl)oxy)methyl)piperidin-1-yl)methyl)tetrahydro-2H-pyran-4-ol;
4-((4-(((4-(Tetrahydro-2H-pyran-4-yl)oxy)benzo[d]isoxazol-3-yl)oxy)methyl)piperidin-1-yl)methyl)tetrahydro-2H-pyran-4-ol;
4-((4-(((4-Isobutoxybenzo[d]isoxazol-3-yl)oxy)methyl)piperidin-1-yl)methyl)tetrahydro-2H-pyran-4-ol;
N-(cis-6-(((4-Hydroxytetrahydro-2H-pyran-4-yl)methyl)piperidin-3-yl)-1-isopropyl-1H-indazole-3-carboxamide;
N-(cis-6-(2-Hydroxy-2-methylpropyl)piperidin-3-yl)-1-isopropyl-1H-indazole-3-carboxamide;
1-Cyclobutyl-N-(cis-6-[(4-hydroxytetrahydro-2H-pyran-4-yl)methyl]piperidin-3-yl)-1H-indazole-3-carboxamide;
N-((3S,5S)-5-(2-Hydroxy-2-methylpropyl)pyrrolidin-3-yl)-1-isopropyl-1H-indazole-3-carboxamide;
5-Fluoro-N-((3S,5S)-5-(2-hydroxy-2-methylpropyl)pyrrolidin-3-yl)-1-isopropyl-1H-indazole-3-carboxamide;
N-((3S,5S)-5-[(1-Hydroxycyclohexyl)methyl]pyrrolidin-3-yl)-1-isopropyl-1H-indazole-3-carboxamide;
4-Amino-5-chloro-N-((1-((1,4-dihydroxycyclohexyl)methyl)piperidin-4-yl)methyl)-2,3-dihydrobenzofuran-7-carboxamide;
4-Amino-5-chloro-N-((1-((4-hydroxytetrahydro-2H-pyran-4-yl)methyl)piperidin-4-yl)methyl)-2,3-dihydrobenzofuran-7-carboxamide;
4-Amino-5-chloro-N-((1-((1,4-dihydroxycyclohexyl)methyl)piperidin-4-yl)methyl)-2-ethoxybenzamide;
4-Amino-5-chloro-2-ethoxy-N-((1-((4-hydroxytetrahydro-2H-pyran-4-yl)methyl)piperidin-4-yl)methyl)benzamide;
4-Amino-5-chloro-N-((1-((1,4-dihydroxycyclohexyl)methyl)piperidin-4-yl)methyl)-2-methoxybenzamide;
4-Amino-5-chloro-N-((1-(((4-hydroxytetrahydro-2H-pyran-4-yl)methyl)piperidin-4-yl)methyl)-2-methoxybenzamide;
5-Amino-6-bromo-N-((1-((tetrahydro-2H-pyran-4-yl)methyl)piperidin-4-yl)methyl)chroman-8-carboxamide;
4-Amino-5-chloro-N-((1-((tetrahydrofuran-2-yl)methyl)piperidin-4-yl)methyl)benzofuran-7-carboxamide;
8-Amino-7-chloro-N-((1-((tetrahydrofuran-2-yl)methyl)piperidin-4-yl)methyl)-2,3-dihydrobenzo[b][1,4]dioxine-5-carboxamide;
(S)-5-Amino-6-chloro-N-((1-((tetrahydrofuran-2-yl)methyl)piperidin-4-yl)methyl)chroman-8-carboxamide;
(S)-4-Amino-5-chloro-2-methoxy-N-((1-((tetrahydrofuran-2-yl)methyl)piperidin-4-yl)methyl)benzamide;
(R)-4-Amino-5-chloro-2-methoxy-N-((1-((tetrahydrofuran-2-yl)methyl)piperidin-4-yl)methyl)benzamide;
(S)-4-Amino-5-chloro-N-((1-((tetrahydrofuran-2-yl)methyl)piperidin-4-yl)methyl)benzofuran-7-carboxamide;
(R)-4-Amino-5-chloro-N-((1-((tetrahydrofuran-2-yl)methyl)piperidin-4-yl)methyl)benzofuran-7-carboxamide;
(S)-5-Amino-6-chloro-N-((1-((tetrahydrofuran-3-yl)methyl)piperidin-4-yl)methyl)chroman-8-carboxamide;
(R)-5-Amino-6-chloro-N-((1-((tetrahydrofuran-3-yl)methyl)piperidin-4-yl)methyl)chroman-8-carboxamide;
(S)-8-Amino-7-chloro-N-((1-((tetrahydrofuran-2-yl)methyl)piperidin-4-yl)methyl)-2,3-dihydrobenzo[b][1,4]dioxine-5-carboxamide;
(R)-8-Amino-7-chloro-N-((1-((tetrahydrofuran-2-yl)methyl)piperidin-4-yl)methyl)-2,3-dihydrobenzo[b][1,4]dioxine-5-carboxamide; and
4-Amino-5-chloro-N-((1-((tetrahydro-2H-pyran-4-yl)methyl)piperidin-4-yl)methyl)benzofuran-7-carboxamide,
or a pharmaceutically acceptable salt thereof.

Several compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The subject invention also includes isotopically-labelled compounds, which are identical to those recited in formula (I), but for the fact that one or more atoms can be replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as 2H, 3H, 13C, 14C, 15N, 18O, 17O, 31P, 32P, 35S, 18F, and 36Cl, respectively. Compounds of the present invention, prodrugs thereof, pharmaceutically acceptable esters of said compounds and pharmaceutically acceptable salts of said compounds, of said esters or of said prodrugs which contain the aforementioned isotopes and/or other isotopes of other atoms are within the scope of this invention. Certain isotopically-labelled compounds of the present invention, for example those into which radioactive isotopes such as 3H and 14C are incorporated, are useful in drug and/or substrate tissue distribution assay. Tritiated hydrogen, i.e., 3H, and carbon-14, i.e., 14C, isotopes are particularly preferred for their ease of presentation and detectability. Further, substitution with heavier isotopes such as deuterium, i.e., 2H, can afford therapeutic advantage resulting from greater metabolic stability, for example increased in vivo half-life or reduced dosage requirement and, hence, may be preferred in some circumstances. Isotopically labelled compounds of formula (I) of this invention and prodrugs thereof can generally be prepared by carrying out the procedure disclosed in above-disclosed Schemes and/or Examples and Preparations below, and by substituting a readily available isotopically labelled reagent for a non-isotopically labelled reagent.

The present invention includes salt forms of the compounds (I) as obtained.

Certain compounds of the present invention may be capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine (i.e., N-benzyl-2-phenylethylamine), benzathine (i.e., N,N-dibenzylethylenediamine), choline, diolamine (i.e., diethanolamine), ethylenediamine, glucosamine, glycine, guanidine, guanine, meglumine (i.e., N-methylglucamine), nicotinamide, olamine (i.e., ethanolamine), ornithine, procaine, proline, pyridoxine, serine, tyrosine, valine and tromethamine (i.e., tris or tris(hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate, camsylate, edisylate (i.e., 1,2-ethanedisulfonate), estolate (i.e., laurylsulfate), gluceptate (i.e., glucoheptonate), gluconate, 3-hydroxy-2-naphthoate, xionofoate (i.e., 1-hydroxy-2-naphthoate), isethionate, (i.e., 2-hydroxyethanesulfonate), mucate (i.e., galactarate), 2-naphsylate (i.e., naphthalenesulphonate, stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1.1'-methylene-bis-(2-hydroxy-3-naphthoate). The acid addition salts can be prepared by conventional procedures.

For a review of suitable salts see Berge et al., J. Pharm. Sci., 66, 1-19, 1977.

Also included within the scope of this invention are bioprecursors (also called "prodrugs") of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, an animal subject including a mammalian subject, e.g., a human subject.

For example, it is possible to make a bioprecursor of the compounds of formula (I), which include hydroxy groups by making an ester of the hydroxy group. When a compound of the formula (I) includes one hydroxy group, only mono-ester is possible. When a compound of the formula (I) includes two hydroxy, mono- and di-esters (which can be the same or different) can be made. When a compound of the formula (I) includes one or two carboxyl groups, mono- and di-esters (which can be the same or different) can be made. Typical esters are simple alkanoate esters, such as acetate, propionate, butyrate, etc. In addition, when a compound of the formula (I) includes a hydroxy group, bioprecursors can be made by converting the hydroxy group to an acyloxy derivative (e.g., a pivaloyloxy derivative) by reaction with an acyl halide (e.g., pivaloyl chloride).

Other typical prodrugs which are well known to those skilled in the art include the preparation of phosphates, amides, esters, thioesters, carbonates, and carbamates. Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

When the compounds of the formula (I) of this invention may form solvates such as hydrates, such solvates are included within the scope of this invention.

For treating or preventing dementia, a suitable dosage level of the compound of this invention is about 0.1 to 400 mg per day, preferably about 0.5 to 40 mg per day, and more preferably about 1 to 10 mg per day, of the active compound. The compounds may be administered on a regimen of 1 to 4 times per day. In some cases, however, a dosage outside these limits may be used.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matters or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

These compounds as 5-HT4 receptor agonists are disclosed in WO2005049608, WO2005073222, WO2006090224, WO2007010390, WO 2006/090279, WO2005021539, WO2007048623, WO2007068739, and WO2007096352. However, the working examples for the treatment of dementia are not disclosed in these literatures.

Also, the present invention provides a pharmaceutical composition for the treatment of dementia in an animal subject including a mammalian subject, which comprises administering to said subject a therapeutically effective amount of a compound of formula (I) or pharmaceutically acceptable salts thereof.

Further, the present invention also provides a pharmaceutical composition for the treatment of dementia, which comprises a therapeutically effective amount of the quinolonecarboxylic acid compound of formula (I) or its pharmaceutically acceptable salt together with a pharmaceutically acceptable carrier.

The invention also provides a method of treating dementia, or preventing or delaying the onset or the progression of dementia, by administering a therapeutically effective amount of the compounds of this invention as defined above or a pharmaceutically acceptable salt thereof to a patient or an animal subject including a mammalian subject in need thereof, wherein dementia is associated with the augmentation of Abeta and/or depletion of ACh levels in the brain.

In a further aspect, the invention provides the use of the compounds of this invention as defined above, or a pharmaceutically acceptable salt thereof, in the manufacture of a medicament for treating dementia, or preventing or delaying the onset or the progression of dementia.

The use of some drugs is restricted in a certain stage of AD. For example, mementin is only used at the severe stage of AD, whereas the compounds of this invention can be used for patients at any stages of AD (mild stage, moderate stage and severe stage).

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine), anti-histamine (e.g. dimebon, The Lancet, 372 (2008) 207-215), 5-HT6 antagonists (Neurotherapeutics, 5 (2008) 458-469) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as statins, e.g. simvastatin. Such additional compounds similarly include compounds known to modify the production or processing of Abeta in the brain ("amyloid modifiers"), such as compounds which inhibit the secretion of Abeta (including gamma-secretase inhibitors, beta-secretase inhibitors, and GSK-3alpha inhibitors), compounds which inhibit the aggregation of Abeta, and antibodies which selectively bind to Abeta. Such additional compounds also include growth hormone secretagogues, as disclosed in WO 2004/110443.

EXAMPLES

Compounds list:
N-((1-((1-(2H-Tetrazol-5-yl)cyclopentyl)methyl)piperidin-4-yl)methyl)-3-isopropyl-2-oxo-2,3-dihydro-1H-benzo[d]imidazole-1-carboxamide;

3-isopropyl-N-((1-(2-Methyl-2-(2H-tetrazol-5-yl)propyl)piperidin-4-yl)methyl)-2-oxo-2,3-dihydro-1H-benzo[d]imidazole-1-carboxamide;

N-((1-((1-(2H-Tetrazol-5-yl)cyclopentyl)methyl)piperidin-4-yl)methyl)-2'-oxospiro[cyclopentane-1,3'-indoline]-1'-carboxamide;

N-((1-((4-hydroxytetrahydro-2H-pyran-4-yl)methyl)piperidin-4-yl)methyl)-3-isopropyl-2-oxo-2,3-dihydro-1H-benzo[d]imidazole-1-carboxamide (Compound A);

5-Fluoro-N-((1-(((4-hydroxytetrahydro-2H-pyran-4-yl)methyl)piperidin-4-yl)methyl)-1-isopropyl-2-oxo-1,2-dihydroquinoline-3-carboxamide;

5-Chloro-N-((1-((4-hydroxytetrahydro-2H-pyran-4-yl)methyl)piperidin-4-yl)methyl)-1-isopropyl-2-oxo-1,2-dihydroquinoline-3-carboxamide;

N-((1-((4-Hydroxytetrahydro-2H-pyran-4-yl)methyl)piperidin-4-yl)methyl)-1-isopropyl-5-methyl-2-oxo-1,2-dihydroquinoline-3-carboxamide;

N-((1-((trans-1,4-Dihydroxycyclohexyl)methyl)piperidin-4-yl)methyl)-1-isopropyl-5-methyl-2-oxo-1,2-dihydroquinoline-3-carboxamide;

N-((1-((cis-1,4-Dihydroxycyclohexyl)methyl)piperidin-4-yl)methyl)-1-isopropyl-5-m ethyl-2-oxo-1,2-dihydroquinoline-3-carboxamide;

5-Bromo-N-((1-(((4-hydroxytetrahydro-2H-pyran-4-yl)methyl)piperidin-4-yl)methyl)-1-isopropyl-6-methyl-2-oxo-1,2-dihydropyridine-3-carboxamide oxalate;

5-Chloro-N-((1-(((trans-1,4-dihydroxy-4-methylcyclohexyl)methyl)piperidin-4-yl)methyl)-1-isopropyl-6-methyl-2-oxo-1,2-dihydropyridine-3-carboxamide;

5-Chloro-N-((1-(((trans-1-hydroxy-4-methoxycyclohexyl)methyl)piperidin-4-yl)methyl)-1-isopropyl-6-methyl-2-oxo-1,2-dihydropyridine-3-carboxamide;

5-Chloro-N-((1-((cis-1-hydroxy-4-methoxycyclohexyl)methyl)piperidin-4-yl)methyl)-1-isopropyl-6-methyl-2-oxo-1,2-dihydropyridine-3-carboxamide;

5-Chloro-N-((1-((1-hydroxycyclohexyl)methyl)piperidin-4-yl)methyl)-1-isopropyl-6-methyl-2-oxo-1,2-dihydropyridine-3-carboxamide;

5-Chloro-N-((1-(cyclohexylmethyl)piperidin-4-yl)methyl)-1-isopropyl-6-methyl-2-oxo-1,2-dihydropyridine-3-carboxamide;

5-Fluoro-N-((1-(((4-hydroxytetrahydro-2H-pyran-4-yl)methyl)piperidin-4-yl)methyl)-1-isopropyl-6-methyl-2-oxo-1,2-dihydropyridine-3-carboxamide;

5-Bromo-N-((1-(((4-hydroxytetrahydro-2H-pyran-4-yl)methyl)piperidin-4-yl)methyl)-1-isopropyl-6-methyl-2-oxo-1,2-dihydropyridine-3-carboxamide;

N-((1-(((4-Hydroxytetrahydro-2H-pyran-4-yl)methyl)piperidin-4-yl)methyl)-1-isopropyl-5,6-dimethyl-2-oxo-1,2-dihydropyridine-3-carboxamide;

5-Chloro-N-((1-(((4-hydroxytetrahydro-2H-pyran-4-yl)methyl)piperidin-4-yl)methyl)-1-isopropyl-6-methyl-2-oxo-1,2-dihydropyridine-3-carboxamide;

4-((4-(((4-((trans-4-Hydroxycyclohexyl)oxy)benzo[d]isoxazol-3-yl)oxy)methyl)piperidin-1-yl)methyl)tetrahydro-2H-pyran-4-ol;

4-((4-(((4-(((1S,2R)-2-Hydroxycyclohexyl)oxy)benzo[d]isoxazol-3-yl)oxy)methyl)piperidin-1-yl)methyl)tetrahydro-2H-pyran-4-ol;

4-((4-(((4-(((1R,3R)-3-Hydroxycyclopentyl)oxy)benzo[d]isoxazol-3-yl)oxy)methyl)piperidin-1-yl)methyl)tetrahydro-2H-pyran-4-ol;

4-((4-(((4-(((1S,2R)-2-Methoxycyclopentyl)oxy)benzo[d]isoxazol-3-yl)oxy)methyl)piperidin-1-yl)methyl)tetrahydro-2H-pyran-4-ol;

4-((4-(((4-(((1S,2R)-2-Hydroxycyclopentyl)oxy)benzo[d]isoxazol-3-yl)oxy)methyl)piperidin-1-yl)methyl)tetrahydro-2H-pyran-4-ol;

4-((4-(((4-(((1R,2R)-2-Methoxycyclopentyl)oxy)benzo[d]isoxazol-3-yl)oxy)methyl)piperidin-1-yl)methyl)tetrahydro-2H-pyran-4-ol;

4-((4-(((4-(((1R,2R)-2-Hydroxycyclopentyl)oxy)benzo[d]isoxazol-3-yl)oxy)methyl)piperidin-1-yl)methyl)tetrahydro-2H-pyran-4-ol;

4-((4-(((4-(((1-Hydroxycyclopentyl)methoxy)benzo[d]isoxazol-3-yl)oxy)methyl)piperidin-1-yl)methyl)tetrahydro-2H-pyran-4-ol;

4-((4-(((4-(Tetrahydro-2H-pyran-4-yl)oxy)benzo[d]isoxazol-3-yl)oxy)methyl)piperidin-1-yl)methyl)tetrahydro-2H-pyran-4-ol;

4-((4-(((4-Isobutoxybenzo[d]isoxazol-3-yl)oxy)methyl)piperidin-1-yl)methyl)tetrahydro-2H-pyran-4-ol;

N-(cis-6-(((4-Hydroxytetrahydro-2H-pyran-4-yl)methyl)piperidin-3-yl)-1-isopropyl-1H-indazole-3-carboxamide;

N-(cis-6-(2-Hydroxy-2-methylpropyl)piperidin-3-yl)-1-isopropyl-1H-indazole-3-carboxamide;

1-Cyclobutyl-N-(cis-6-[(4-hydroxytetrahydro-2H-pyran-4-yl)methyl]piperidin-3-yl)-1H-indazole-3-carboxamide;

N-((3S,5S)-5-(2-Hydroxy-2-methylpropyl)pyrrolidin-3-yl)-1-isopropyl-1H-indazole-3-carboxamide;

5-Fluoro-N-((3S,5S)-5-(2-hydroxy-2-methylpropyl)pyrrolidin-3-yl)-1-isopropyl-1H-indazole-3-carboxamide;

N-((3S,5S)-5-[(1-Hydroxycyclohexyl)methyl]pyrrolidin-3-yl)-1-isopropyl-1H-indazole-3-carboxamide;

4-Amino-5-chloro-N-((1-((1,4-dihydroxycyclohexyl)methyl)piperidin-4-yl)methyl)-2,3-dihydrobenzofuran-7-carboxamide;

4-Amino-5-chloro-N-((1-(((4-hydroxytetrahydro-2H-pyran-4-yl)methyl)piperidin-4-yl)methyl)-2,3-dihydrobenzofuran-7-carboxamide;

4-Amino-5-chloro-N-((1-((1,4-dihydroxycyclohexyl)methyl)piperidin-4-yl)methyl)-2-ethoxybenzamide;

4-Amino-5-chloro-2-ethoxy-N-((1-((4-hydroxytetrahydro-2H-pyran-4-yl)methyl)piperidin-4-yl)methyl)benzamide;

4-Amino-5-chloro-N-((1-((1,4-dihydroxycyclohexyl)methyl)piperidin-4-yl)methyl)-2-methoxybenzamide;

4-Amino-5-chloro-N-((1-(((4-hydroxytetrahydro-2H-pyran-4-yl)methyl)piperidin-4-yl)methyl)-2-methoxybenzamide;

5-Amino-6-bromo-N-((1-((tetrahydro-2H-pyran-4-yl)methyl)piperidin-4-yl)methyl)chroman-8-carboxamide;

4-Amino-5-chloro-N-((1-((tetrahydrofuran-2-yl)methyl)piperidin-4-yl)methyl)benzofuran-7-carboxamide;

8-Amino-7-chloro-N-((1-((tetrahydrofuran-2-yl)methyl)piperidin-4-yl)methyl)-2,3-dihydrobenzo[b][1,4]dioxine-5-carboxamide;

(S)-5-Amino-6-chloro-N-((1-((tetrahydrofuran-2-yl)methyl)piperidin-4-yl)methyl)chroman-8-carboxamide;

(S)-4-Amino-5-chloro-2-methoxy-N-((1-((tetrahydrofuran-2-yl)methyl)piperidin-4-yl)methyl)benzamide;

(R)-4-Amino-5-chloro-2-methoxy-N-((1-((tetrahydrofuran-2-yl)methyl)piperidin-4-yl)methyl)benzamide;

(S)-4-Amino-5-chloro-N-((1-((tetrahydrofuran-2-yl)methyl)piperidin-4-yl)methyl)benzofuran-7-carboxamide;

(R)-4-Amino-5-chloro-N-((1-((tetrahydrofuran-2-yl)methyl)piperidin-4-yl)methyl)benzofuran-7-carboxamide;

(S)-5-Amino-6-chloro-N-((1-((tetrahydrofuran-3-yl)methyl)piperidin-4-yl)methyl)chroman-8-carboxamide;

(R)-5-Amino-6-chloro-N-((1-((tetrahydrofuran-3-yl)methyl)piperidin-4-yl)methyl)chroman-8-carboxamide;

(S)-8-Amino-7-chloro-N-((1-((tetrahydrofuran-2-yl)methyl)piperidin-4-yl)methyl)-2,3-dihydrobenzo[b][1,4]dioxine-5-carboxamide;

(R)-8-Amino-7-chloro-N-((1-((tetrahydrofuran-2-yl)methyl)piperidin-4-yl)methyl)-2,3-dihydrobenzo[b][1,4]dioxine-5-carboxamide; and 4-Amino-5-chloro-N-((1-((tetrahydro-2H-pyran-4-yl)methyl)piperidin-4-yl)methyl)benzofuran-7-carboxamide.

Example 1

Rat Novel Object Recognition Study (Method Referred: PNAS, 101 (2003) 853-858)

Male IGS rats (9 weeks-old, Charles River Laboratories Japan, Inc.) were used in this study. Compound A and donepezil hydrochloride (reference substance) were orally administered at 60 min before training trial and before retention trial. Number of animals per group was 15. Open-field box (40×40×40 cm) with sawdust covering its floor was used in this study. As for the training trials, the animals were allowed to explore two identical objects (A1 and A2) for 3 min. The objects are plastic "LEGO bricks" that vary in shape, color, and size. An overhead camera and a DVD recorder were used to monitor and record the animal's behavior. The retention trials were conducted 24 hr after the training trial. One copy of the familiar object (A3) and a novel object (B) were placed in the same location as in the training trial, and the animals were allowed to explore the objects for 3 min. An overhead camera and a DVD recorder were used to monitor and record the animal's behavior.

Exploration of an object was defined as pointing the nose to the object at a distance of <1 cm and/or touching it with the nose. DVD images were analyzed by an observer who was not unaware of the treatment condition. To assess cognitive performance, the time spent exploring the familiar (TA3) and novel (TB) object, and discrimination index (DI; (TB−TA3)/(TB+TA3)) was analyzed. Pro-cognitive effect was defined as increased DI, and increased TB and/or decreased TA3. To assess the overall levels of exploratory performance, total time spent exploring the both objects was analyzed.

For Compound A, discrimination index was analyzed using Bartlett's test followed by Dunnett's multiple comparison test. Discrimination index in 0.1, 0.3, 1 mg/kg Compound A-treated groups was statistically significant compared to that in vehicle-treated group (*$p<0.05$, **$p<0.01$). For donepezil, discrimination index was analyzed using F-test, followed by Student's t-test. Discrimination index in donepezil-treated group was statistically significant compared to that in vehicle-treated group ($^\#p<0.05$) (see FIG. 1).

The compounds described in the compounds list are similarly conducted in this novel object recognition study in rats. Improvement of discrimination index is observed in all cases.

Example 2

Spontaneous Alteration Test in Rats (Method Referred: Eur. J. Pharmacol., 236 (1993) 341-345)

Male IGS rats (6 weeks-old, Charles River Laboratories Japan, Inc.) were used in this study. The scopolamine solution or saline was administered intraperitoneally 30 minutes after the administration of the test substance or vehicle. Thirty minutes after the injection, the rat was placed at the end of one arm toward to the end of the arm and was allowed to move freely through the maze for 8-min test session. The sequence of arm entries was recorded manually. Alteration was defined as entry into all three arms on consecutive choices. The percent alteration as an indicator of spontaneous alteration performance was calculated as (number of alterations/total number of arm entries minus 2)×100.

Figure 2:
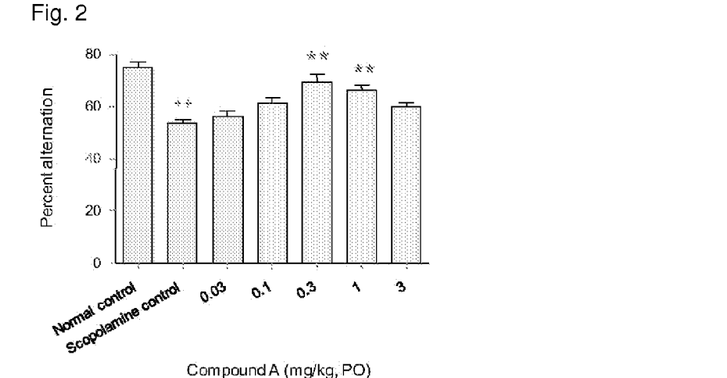
FIG. 2 is a graph showing restore of spontaneous alteration.

The effect of Compound A on the scopolamine-induced impairment of spontaneous alteration performance in rats was investigated. In the percent alterations, the values on saline- and scopolamine-treated groups were 75.2% and 53.9%, respectively. The percent alteration was significantly reduced by scopolamine injection (p<0.01). Compound A at doses of 0.3 and 1 mg/kg significantly increased the percent alterations when compared to vehicle-treated group (p<0.01). Compound A at 0.1 and 3 mg/kg showed a tendency to improve without statistical significance (see FIG. 2).

The compounds described in the compounds list are similarly conducted in this spontaneous alteration test in rats. Restore of spontaneous alteration is observed in all cases.

Example 3

Abeta Reduction in Tg2576 Mice (Method Referred: J. Neurosci 21 (2001) 372-381)

Female Tg2576 mice that express the human amyloid precursor protein (APP) gene with the Swedish mutation ($APP_{SWE}$) were purchased from Taconic Farms (catalog #001349-TF).

Tg2576 mice (31-week old at the beginning of the experiment) were dosed orally twice a day (BID) for 3 weeks with 0.1, 1, or 10 mg/kg Compound A in the vehicle consisting of 0.5% methylcellulose and 0.1% Tween 80. Mice were euthanized three hours after the last dose. Brain tissues were collected and homogenized in 5-volumes of ice-cold TBS buffer (50 mM Tris-HCl) containing 1% CHAPS and protease inhibitors. The homogenates were centrifuged at 14,000 g for 10 minutes at 4° C., and the resulting supernatants were collected as soluble pool of Abeta. The pellets were dissolved in the starting volume of 5 M guanidine in TBS buffer and the resulting homogenates were collected as insoluble pool of Abeta. Abeta1-40 and Abeta1-42 were quantified using commercially available ELISA kits according to the manufacture's instructions. Measurements were performed in duplicate. The final values of Abeta in the brain were expressed as nanograms per gram wet brain weight. Total Abeta levels were obtained by adding the values of the soluble and insoluble Abeta levels.

Figure 3:
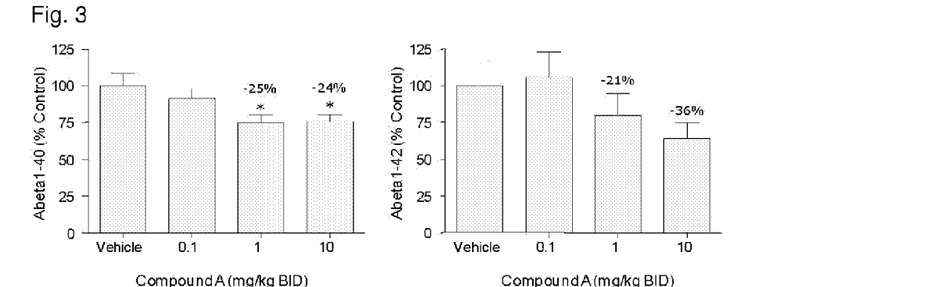
FIG. 3 is a graph showing Abeta (Abeta1-40 (left side) or 1-42 (right side)) reduction in Tg2576 mice.

The results are summarized in FIG. 3. Three-week administration of Compound A at doses of 1 and 10 mg/kg BID significantly decreased total brain Abeta1-40 levels and also dose-dependently and substantially decreased total brain Abeta1-42 levels in Tg2576 mice.

The compounds described in the compounds list are similarly conducted in this Abeta reduction in Tg2576 mice. Abeta reduction is observed in all cases.

Example 4

Increase of Hippocampus ACh Release in Rats

Effects of Compound A on rat hippocampus (Hip) ACh level were tested using microdialysis in Male Wistar rats. One day before the start of the experiments, rats were anesthetized and guide cannula was implanted in the dorsal Hip. One day after surgery, a dialysis probe was inserted through a guide cannula in Hip and perfused with artificial cerebrospinal fluid (aCSF) containing 148 mM NaCl, 2.7 mM KCl, 1.2 mM $CaCl_2$, 0.85 mM $MgCl_2$, together with 100 nM eserine. After a 1 h equilibration period, sample collection began. Outflow fractions were collected every 20 min. After six stable baseline fractions were collected, the perfusate was replaced to aCSF containing Compound A with 100 nM eserine for 120 min, and then it was switched again to aCSF with 100 nM eserine alone. Dialysis fractions were then analyzed using high performance liquid chromatography with an electrochemical detection system. Isopropyl homocholine was used as internal standard. The amount of ACh in each dialysate sample was calculated from the peak height ratio of ACh/IPHC. ACh content was expressed as a percent of baseline calculated from the average of three samples preceding drug infusion.

Figure 4:
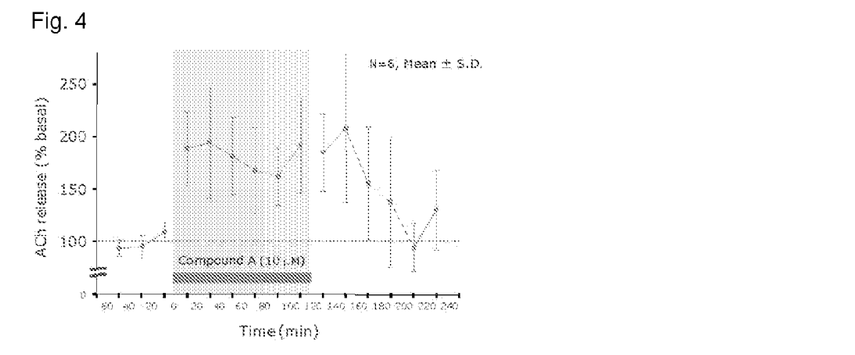
FIG. 4 is a graph showing ACh concentration in rat hippocampus (N=6).

The results are summarized in FIG. 4. Direct injection of Compound A into rat Hip increased ACh concentration at 187%.

The compounds described in the compounds list are similarly conducted this ACh microdialysis study. Increase of ACh level is observed in all cases.

REFERENCE TO FIGS. 1 TO 4

(FIG. 1)
Discrimination index is defined as the difference in exploration on time for the objects divided by total exploration time.

Figure 1:
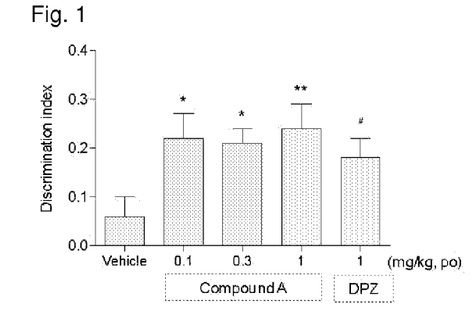
FIG. 1 is a graph showing improvement of discrimination index of Novel Object Recognition Test.

Compound A: discrimination index was analyzed using Bartlett's test, followed by Dunnett's multiple comparison test (*p<0.05, **p<0.01 vs. vehicle).

For Donepezil (DPZ), discrimination index was analyzed using F-test, followed by Student's t-test ($^\#$p<0.05 vs. vehicle).

(FIG. 2)
N=15, Mean±S.E.M
$^{++}$p<0.01; vs. Normal control (Student's t-test)
**p<0.01; vs. Scopolamine control (Dunnett's test)
No significant change of total arm entry between each treatment group was observed.

(FIG. 3)
Vehicle, 1 and 10 mg/kg arm (N=10), 0.1 mg/kg arm (N=9), Mean±S.E.M
*p<0.05; one-way ANOVA followed by Dunnett's post hoc analysis (FIG. 4)
ACh content was expressed as a percent of baseline calculated from the average of three samples preceding drug infusion.

INDUSTRIAL APPLICABILITY

According to the present invention, a compound of formula (I) or a pharmaceutically acceptable salt thereof is useful for the treatment of dementia.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:
1. A method for the treatment of a disease selected from the group consisting of Alzheimer's Disease, Parkinson's Disease-related dementia, Diffuse Lewy body-related dementia,

Down syndrome-related dementia, HIV-related dementia, and depression-associated dementia in animal subjects suffering therefrom by decreasing total brain beta-amyloid peptide (Abeta) by administration of N-((1-(((4-hydroxytetrahydro-2H-pyran-4-yl)methyl)piperidin-4-yl)methyl)-3-isopropyl-2-oxo-2,3-dihydro-1H-benzo[d]imidazole-1-carboxamide or a pharmaceutically acceptable salt thereof to decrease total brain beta-amyloid peptide (Abeta).

2. The method of claim 1, which further comprises administering a therapeutically effective amount of one or more additional compounds known to be useful in the treatment or prevention of dementia.

3. The method according to claim 1, wherein the Abeta is Abeta 1-40 or Abeta 1-42.

* * * * *